US012334191B2

(12) United States Patent
Ball et al.

(10) Patent No.: US 12,334,191 B2
(45) Date of Patent: *Jun. 17, 2025

(54) HAPLOTYPE PHASING MODELS

(71) Applicant: Ancestry.com DNA, LLC, Lehi, UT (US)

(72) Inventors: Catherine Ann Ball, Mountain View, CA (US); Keith D. Noto, San Francisco, CA (US); Kenneth G. Chahine, Park City, UT (US); Mathew J. Barber, Chicago, IL (US); Yong Wang, Foster City, CA (US)

(73) Assignee: Ancestry.com DNA, LLC, Lehi, UT (US)

(*) Notice: Subject to any disclaimer, the term of this patent is extended or adjusted under 35 U.S.C. 154(b) by 1192 days.

This patent is subject to a terminal disclaimer.

(21) Appl. No.: 16/862,266

(22) Filed: Apr. 29, 2020

(65) Prior Publication Data
US 2020/0303035 A1 Sep. 24, 2020

Related U.S. Application Data

(63) Continuation of application No. 15/519,099, filed as application No. PCT/US2015/056164 on Oct. 19, 2015, now Pat. No. 10,679,729.

(60) Provisional application No. 62/065,726, filed on Oct. 19, 2014, provisional application No. 62/065,557, filed on Oct. 17, 2014.

(51) Int. Cl.
G16B 20/20 (2019.01)
G06F 17/18 (2006.01)
G16B 5/00 (2019.01)
G16B 5/20 (2019.01)
G16B 20/00 (2019.01)
G16B 40/00 (2019.01)
G16B 40/20 (2019.01)
G16B 40/30 (2019.01)

(52) U.S. Cl.
CPC .............. G16B 20/20 (2019.02); G06F 17/18 (2013.01); G16B 5/00 (2019.02); G16B 5/20 (2019.02); G16B 20/00 (2019.02); G16B 40/00 (2019.02); G16B 40/20 (2019.02); G16B 40/30 (2019.02)

(58) Field of Classification Search
CPC ........ G16B 40/20; G16B 20/00; G16B 40/00; G16B 20/20; G16B 30/00; G16B 45/00; G16B 5/20; G16B 50/10; G16B 50/30; G16B 30/10; G16B 50/00; G06N 7/01; G06N 3/09; G06N 3/0895; C12Q 1/6827; C12Q 2537/165; C12Q 2600/172; C12Q 2600/156; G06F 17/18; G06F 16/248; G06F 16/22; C12N 2320/34; G06T 11/206; G06T 2200/24; G06T 2207/20084
See application file for complete search history.

(56) References Cited

U.S. PATENT DOCUMENTS

| | | | |
|---|---|---|---|
| 8,463,554 B2 | 6/2013 | Hon et al. | |
| 8,510,057 B1 | 8/2013 | Avey et al. | |
| 9,213,944 B1 | 12/2015 | Do et al. | |
| 9,213,947 B1 | 12/2015 | Do et al. | |
| 9,367,800 B1 | 6/2016 | Do et al. | |
| 9,836,576 B1 | 12/2017 | Do et al. | |
| 10,504,611 B2 * | 12/2019 | Granka | G16B 20/00 |
| 10,679,729 B2 * | 6/2020 | Ball | G06F 17/18 |
| 12,148,507 B2 * | 11/2024 | Granka | G16B 5/00 |
| 2002/0143578 A1 | 10/2002 | Cole et al. | |
| 2003/0059808 A1 | 3/2003 | Liu et al. | |
| 2003/0113727 A1 | 6/2003 | Girn et al. | |
| 2004/0175702 A1 | 9/2004 | Magness et al. | |
| 2008/0027656 A1 | 1/2008 | Parida | |
| 2008/0154566 A1 | 6/2008 | Myres et al. | |
| 2008/0255768 A1 | 10/2008 | Martin et al. | |
| 2012/0283108 A1 | 11/2012 | Sampas | |
| 2013/0085728 A1 | 4/2013 | Tang et al. | |

(Continued)

FOREIGN PATENT DOCUMENTS

WO  WO 2012/099890 A1  7/2012
WO  WO 2014/145280 A1  9/2014

(Continued)

OTHER PUBLICATIONS

Bonnen, P. E et al., "The International HapMap 3 Consortium . . . Integrating common and rare genetic variation in diverse human populations," Nature, 2010, vol. 467, pp. 52-58.

(Continued)

Primary Examiner — Mary K Zeman
(74) Attorney, Agent, or Firm — Fenwick & West LLP

(57) ABSTRACT

Novel haplotype cluster Markov models are used to phase genomic samples. After the models are built, they rapidly and accurately phase new samples without requiring that the new samples be used to re-build the models. The models set transition probabilities such that the probability for an appearance of any allele within any haplotype is a non-zero number. Furthermore, the most unlikely pairs of haplotypes are discarded from each model at each level until ε of the likelihood mass at each level is discarded. The models are also constructed such that contributing windows of SNPs partially overlap so that phasing decisions near one of the extreme ends of any model is are not significantly determinative of the phase. Additionally, the models are configured such that two or more nodes can be merged during the building/updating procedure to consolidate haplotype clusters having similar distributions.

20 Claims, 7 Drawing Sheets

(56) References Cited

U.S. PATENT DOCUMENTS

| | | |
|---|---|---|
| 2013/0123120 A1 | 5/2013 | Zimmermann et al. |
| 2013/0297221 A1 | 11/2013 | Johnson et al. |
| 2014/0045705 A1 | 2/2014 | Bustamante et al. |
| 2014/0067355 A1 | 3/2014 | Noto et al. |
| 2014/0278138 A1 | 9/2014 | Barber et al. |
| 2016/0026755 A1 | 1/2016 | Byrnes et al. |
| 2020/0098445 A1 | 3/2020 | Granka et al. |

FOREIGN PATENT DOCUMENTS

| | | |
|---|---|---|
| WO | WO 2016/061260 A1 | 4/2016 |
| WO | WO 2016/061568 A1 | 4/2016 |

OTHER PUBLICATIONS

Browning, B. L. et al., "A Unified Approach to Genotype Imputation and Haplotype Phase Inference for Large Data sets of Trios and Unrelated Individuals," The American Journal of Human Genetics, Feb. 13, 2009, pp. 210-223, vol. 84.

Browning, B. L. et al., "Improving the Accuracy and Efficiency of Identity by Descent Detection in Population Data," Genetics, Jun. 2013, pp. 459-471, vol. 194.

Browning, B.L et al., "Efficient Multilocus Association Testing for Whole Genome Association Studies Using Localized Haplotype Clustering," Genetic Epidemiology, 2007, vol. 31, pp. 365-375.

Browning, B.L. et al., "A Fast, Powerful Method for Detecting Identity by Descent," The American Journal of Human Genetics, 2011, vol. 88, No. 2, pp. 173-182.

Browning, S. R. Multilocus Association Mapping Using Variable-length Markov Chains. Jun. 2006. The American Journal of Human Genetics, col. 78 pp. 903-913.

Browning, S.R. et al., "Haplotype Phasing: Existing Models and New Developments," Nature Reviews Genetics, Oct. 2011, pp. 703-714, vol. 12.

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.

Browning, S.R. et al., "Rapid and Accurate Haplotype Phasing and Missing-Data Inference for Whole-Genome Association Studies by Use of Localized Haplotype Clustering," The American Journal of Human Genetics, Sep. 21, 2007, pp. 1084-1097, vol. 81, No. 5.

Browning, S.R., "Multilocus Association Mapping Using Variable-Length Markov Chains," American Journal of Human Genetics, Apr. 7, 2006, pp. 903-913, vol. 78, No. 6.

Druet, T., et al., "A Hidden Markov Model Combining Linkage and Linkage Disequilibrium Information for Haplotype Reconstruction and Quantitative Trait Locus Fine Mapping," Genetics, 2010, pp. 789-798, vol. 184, No. 3.

Durand, E.Y. et al., "Reducing Pervasive False-Positive Identical-by-Descent Segments Detected by Large-Scale Pedigree Analysis," Molecular Biology and Evolution, Apr. 30, 2014, pp. 2212-2222, vol. 31, No. 8.

Durbin, R. M. et al., "A Map of Human Genome Variation from Population-Scale Sequencing," Nature, Oct. 28, 2010, pp. 1061-1073, vol. 467.

Elston, R.C. et al., "A General Model for the Genetic Analysis of Pedigree Data," Human Heredity, 1971, pp. 523-542, vol. 21, No. 6.

European Extended Search Report, European Application No. 15850985.1, dated Mar. 6, 2018, 12 pages.

European Extended Search Report, European Application No. 15851471.1, dated Mar. 6, 2018, 12 pages.

Falush, D. et al., "Inference of Population Structure Using Multilocus Genotype Data: Linked Loci and Correlated Allele Frequencies," Genetics Society of America, 2003, vol. 164, pp. 1567-1587.

Gusev A. et al., "Whole Population, Genomewide Mapping of Hidden Relatedness," Genome Research, 2009, pp. 318-326, vol. 19.

Jarvis, J.P. et al., "Patterns of Ancestry, Signatures of Natural Selection, and Genetic Association with Stature in Western African Pygmies," PLoS Genetics, Apr. 2012, vol. 8, No. 4, pp. 1-15.

Kenny, E.E. et al., "Increased Power of Mixed Models Facilitates Association Mapping of 10 Loci for Metabolic Traits in an Isolated Population," Human Molecular Genetics, 2011, oo. 827-839, vol. 20, No. 4.

Kong, A. et al. "Detection of Sharing by Descent, Long-Range Phasing and Haplotype Imputation," Nature Genetics, Sep. 2008, pp. 1068-1075, vol. 40, No. 9.

Lander, E.S. et al., "Construction of Multilocus Genetic Linkage Maps in Humans," Proc. Nat. Acad. Sci., Apr. 1987, pp. 2363-2367, vol. 84.

Li, H. et al., "Relationship Estimation from Whole-Genome Sequence Data," PLOS Genetics, Jan. 30, 2014, e1004144, pp. 1-12, vol. 10, No. 1.

Li, Y. et al., "Haplotype Reconstruction in Large Pedigrees with Untyped Individuals through IBD reference," Journal of Computational Biology, 2011, vol. 18, No. 11, pp. 1411-1421.

Li, Y. et al., "MaCH: Using Sequence and Genotype Data to Estimate Haplotypes and Unobserved Genotype," Genetic Epidemiology, Nov. 5, 2010, pp. 816-834, vol. 34, No. 8.

Livne, O.E. et al., "Fast and Accurate Pedigree-based Imputation from sequence data in a Founder Population," PLOS Computational Biology, 2015, vol. 11, No. 3, pp. 1-14.

Meuwissen, T. et al., "The Use of Family Relationships and Linkage Disequilibrium to Impute Phase and Missing Genotypes in Up to Whole Genome Sequence Density Genotypic Data," Genetics, Aug. 2010, pp. 1441-1449, vol. 185.

Morrison, A.C. et al., "Prediction of Coronary Heart Disease Risk using a Genetic Risk Score: The Atherosclerosis Risk in Communities Study," American Journal of Epidemiology, Apr. 18, 2007, vol. 166, No. 1, pp. 28-35.

Ott, J., "Estimation of the Recombination Fraction in Human Pedigrees: Efficient Computation of the Likelihood for Human Linkage Studies," American Journal of Human Genetics, 1974, pp. 588-597, vol. 26, No. 5.

Palin, K. et al., "Identity-by-Descent based phasing and imputation in Founder populations using graphical models," Genetic Epidemiology, 2011, vol. 35, No. 8, pp. 853-860.

PCT International Search Report & Written Opinion, International Application No. PCT/US2015/056164, dated Jan. 5, 2016, 9 Pages.

Platt, J.C., "Probablistic Outputs for Support Vector Machines and Comparisons to Regularized Likelihood Methods," Microsoft Research, Mar. 26, 2999, pp. 1-11.

Price, A.L. et al., "Sensitive Detection of Chromosomal Segments of Distinct Ancestry in Admixed Populations," PLoS Genetics, Jun. 2009, vol. 5, No. 6, pp. 1-18.

Purcell, S. et al., "Plink: A Tool Set for Whole-Genome Association and Population-Based Linkage Analyses," The American Journal of Human Genetics, Sep. 2007, pp. 559-575, vol. 81.

Rabiner, L., "A Tutorial on Hidden Markov Models and Selected Applications in Speech Recognition," Proceedings of the IEEE, Feb. 1989, pp. 257-286, vol. 77, No. 2.

Rabiner, L.R., "A tutorial on Hidden Markov Models and Selected Applications in Speech Recognition," Proceedings of the IEEE, Feb. 1989, vol. 77, No. 2, pp. 257-286.

Rocchi, M., et al., "Ancestral genomes reconstruction: An integrated, multi-disciplinary approach is needed," Genome Research, 2006, pp. 1441-1444, vol. 16, No. 12.

Ron, D. et al., "On the Learnability and Usage of Acyclic Probabilistic Finite Automata," Journal of Computer and System Sciences, 1998, vol. 56, pp. 133-152.

Ron, D., et al., "On the Learnability and Usage of Acyclic Probabilistic Finite Automata," Journal of Computer and System Sciences, 1998, pp. 133-152, vol. 56.

Scheet, P. et al., "A Fast and Flexible Statistical Model for Large-Scale Population Genotype Data: Applications to Inferring Missing Genotypes and Haplotypic Phase," The American Journal of Human Genetics, Apr. 2006, vol. 78, pp. 629-644.

Seligsohn, M.D. et al., "Genetic Susceptibility to Venous Thrombosis," The New England Journal of Medicine, Apr. 19, 2001, vol. 344, No. 16, pp. 1222-1231.

(56) References Cited

OTHER PUBLICATIONS

Speed, D. et al., "Relatedness in the post-genomic era: is it still useful?" Nature Reviews Genetics, 2015, vol. 16, No. 1, pp. 33-45.
Sundquist, A. et al., "Effect of genetic divergence in identifying ancestral origin using HAPPAA," Genome Research, 2008, vol. 18, pp. 676-682.
Thompson, E. A. "Statistical Inference from Genetic Data on Pedigrees," NSF-CBMS Regional Conference Series in Probability and Statistics, 2000, 186 pages, vol. 6.
Thompson, E.A., "Identity by Descent: Variation in Meiosis, Across Genomes, and in Populations," Genetics, 2013, pp. 301-326, vol. 194.
Tipping, M.E., "Sparse Bayesian Learning and the Relevance Vector Machine," Journal of Machine Learning Research, 2001, vol. 1, pp. 211-244.
U.S. Appl. No. 61/724,228, filed Nov. 8, 2012, Do et al. (copy not enclosed).
United States Office Action, U.S. Appl. No. 15/519,105, dated Apr. 5, 2019, 121 pages.
Weedon, M.N. et al., "Combining Information from Common Type 2 Diabetes Risk Polymorphisms Improves Disease Prediction," PLoS Medicine, Oct. 2006, vol. 3, No. 10, pp. 1877-1882.
Welch, B. L., "The Generalization of "Student's" Problem When Several Different Population Variances are Involved," Biometrika, Jan. 1947, pp. 28-35, vol. 34, Issue 1-2.
Williams, A.L. et al., "Phasing of Many Thousands of Genotyped Samples," American Journal of Human Genetics, Aug. 10, 2012, pp. 238-251, vol. 91, No. 2.
Yang, Q. et al., "Improving the Prediction of Complex Diseases by Testing for Multiple Disease-Susceptibility Genes," American Journal of Human Genetics, 2003, vol. 72, pp. 636-649.
Yoon, B.J., "Hidden Markov Models and their Application in Biological Sequence Analysis," Current Genomics, 2009, vol. 10, pp. 402-415.
United States Office Action, U.S. Appl. No. 15/519,099, filed Oct. 3, 2019, ten pages.
Stevens, E. L. et al. "Inference of Relationships in Population Data Using Identity-by-Descent and Identity-by-State." PLoS Genetics, vol. 7, No. 9, Sep. 2011, pp. 1-15.
United States Office Action, U.S. Appl. No. 16/701,162, filed Sep. 28, 2023, 18 pages.

* cited by examiner

Chromosome 700

Model #7  Model #8

Markov models overlap by about 100 SNPS

FIG. 7A

Given two pairs of phased haplotypes, select a heterozygous site near the middle of the overlap as the switch-over point...

H1 701  1000000111100110111111110000011111 1110111 0111
H2 702  1000000111100001111111111000111111101 0 0000111100
        Haplotype Pair as phased by Model #7
        H3 703  1101 0 0000111100111101111111111111000111111111
        H4 704  1111 1 1101110111111111111111111100100011011111100001
        Haplotype Pair as phased by Model #8

...and use it to decide whether to copy the same top/bottom orientation or the reverse in the final output 1000000111100110111111110000011111111011101111111111111111100100011011111100001
1000000111100001111111111000111111101000011110011111111111111000111111111111111

FIG. 7B

HAPLOTYPE PHASING MODELS

CROSS REFERENCE TO RELATED APPLICATIONS

This application is a continuation of prior, co-pending U.S. application Ser. No. 15/519,099, with a 371(c) date of Apr. 13, 2017, which is a National Stage Entry of International Application No. PCT/US2015/056164, filed Oct. 19, 2015, which claims the benefits of priority to U.S. Provisional Application No. 62/065,726, filed on Oct. 19, 2014 and U.S. Provisional Application No. 62/065,557, filed on Oct. 17, 2014. All of the foregoing are incorporated herein by reference in their entireties for all purposes.

BACKGROUND

Field

The disclosed embodiments relate to models for phasing genomic samples into haplotypes. In particular, the disclosed embodiments relate to phasing algorithms that efficiently and accurately phase genomic samples.

Description of Related Art

Although humans are, genetically speaking, almost entirely identical, small differences in human DNA are responsible for much of the variation between individuals. For example, a sequence variation at one position in DNA between individuals is known as a single-nucleotide polymorphism (SNP). SNPs can serve as biomarkers for heredity and disease studies. Stretches of DNA inherited together from a single chromosome are referred to as haplotypes. Haplotypes are identified based on consecutive SNPs of varying length.

Traditional phasing algorithms separate diploid genotypes into a pair of haplotypes. These algorithms are capable of phasing many genomic samples simultaneously, comparing the genotypes and potential haplotypes to others in the input, and iteratively improving the phase over many iterations of the algorithm. However, known models (Browning S. R. and Browning B. L. Rapid and accurate haplotype phasing and missing-data inference for whole-genome association studies by use of localized haplotype clustering, *American Journal of Human Genetics*, 91:1084-1096, 2007; Ron. D, Singer Y, and Tishby N. On the learnability and usage of acyclic probabilistic finite automata, *J. Comp Syst. Sci.*, 56:133-152, 1998) use phasing algorithms that become intractable when the input contains hundreds of thousands of samples, and new samples must be phased by rebuilding the model using existing (reference) phased samples and new unphased samples. These approaches are not practical for batches of hundreds of thousands of samples, where new samples are continuously being added to each batch. New models and algorithms are needed to efficiently and accurately phase large numbers of genomic samples.

SUMMARY

Disclosed herein are methods for phasing input samples of diploid genotypes. Using a reference set of genomic samples that have already been phased, a number of haplotype cluster Markov models are trained that can be used to phase new samples quickly and accurately. Any new sample can be phased in this manner by updating any existing models by using a Hidden Markov Model analysis to identify new phasing examples to use to update the existing Markov models. There is no need to entirely re-build new haplotype cluster Markov models with the addition of each new sample. This allows for accommodation of continuous or periodic new sample data, regardless of how closely it matches previously built models.

In one embodiment, a process for phasing a set of input diploid genotypes includes accessing a set of reference haplotypes corresponding to reference diploid genotypes that have already been phased. The reference haplotypes are divided into a plurality of windows of sequential single nucleotide polymorphisms (SNPs). A set of Markov models are generated based on the reference haplotypes, where each Markov model based on one of the windows and the SNPs of the reference haplotypes within that window. The set of input diploid genotypes are then used to generate, for each window, a set of pairs of possible haplotype phasings for the diploid genotype based on the Markov model for that window. The corresponding Markov model for each window is updated based on the SNPs for that window from the reference haplotypes and also based on the set of pairs of possible haplotype phasings for that window generated from the input diploid genotypes. This updating process may be repeated multiple times to further train the Markov models. A pair of probable haplotype phasings are then generated for the diploid genotype based on the re-generated Markov model for that window. The pairs of probable haplotype phasings for the windows are combined into a single pair of probable phased haplotypes, and the resulting single pair of probable phased haplotypes for the input sample of the diploid genotype are provided as an output.

BRIEF DESCRIPTION OF THE DRAWINGS

These and other features, aspects, and advantages of the present invention will become better understood with regard to the following description, and accompanying drawings, where:

FIG. 7A illustrates an example of overlapping adjacent windows of SNPs used to generate Markov models M, according to one embodiment.

FIG. 7B illustrates an example of how overlapping windows of phased haplotypes can be used to join the haplotypes across windows.

Figure 1:
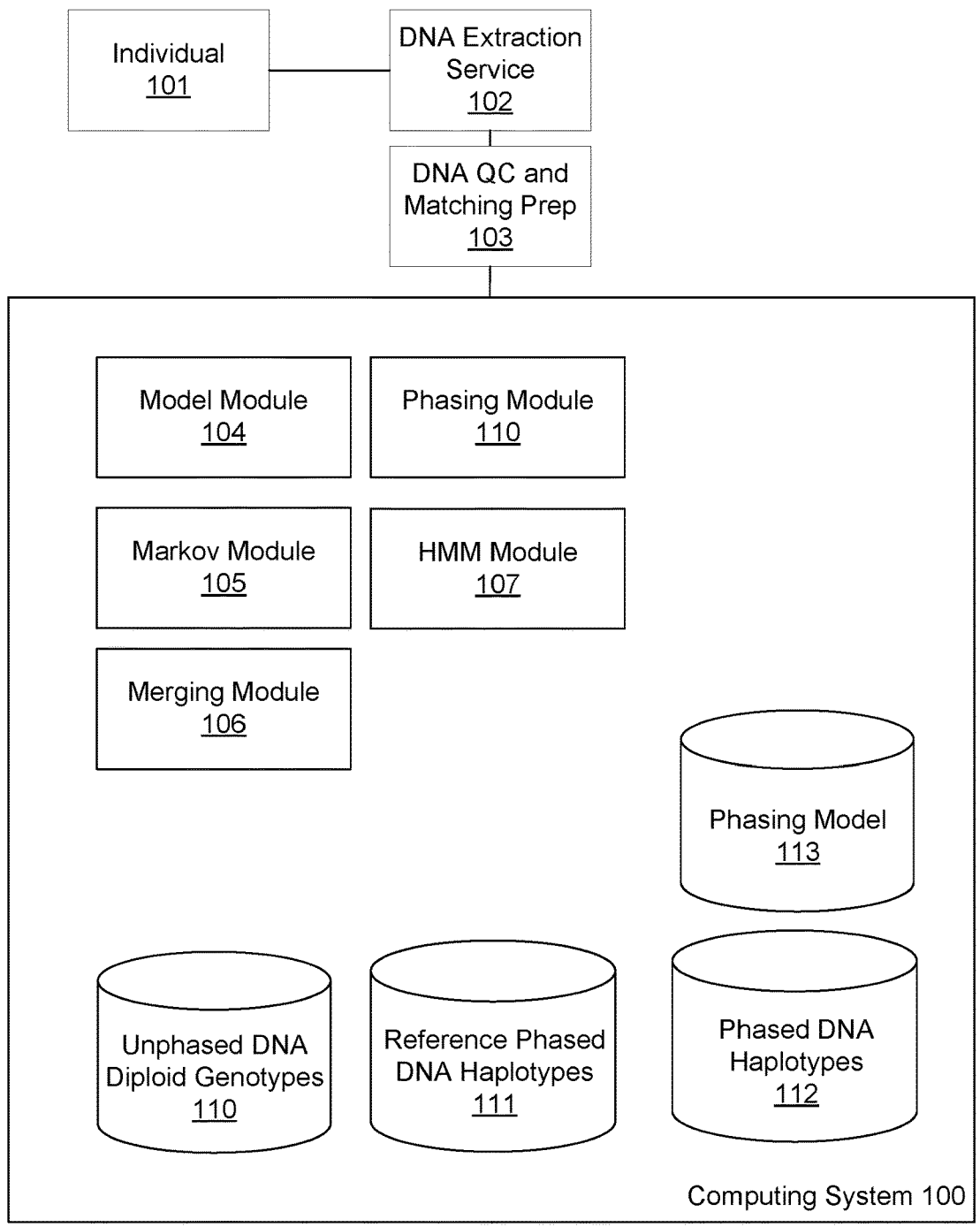
FIG. 1 is a block diagram of a computing environment for training and using a model for phasing diploid genotypes, according to one embodiment.

Note that for purposes of clarity, only one of each item corresponding to a reference numeral is included in most figures, but when implemented multiple instances of any or all of the depicted modules may be employed, as will be appreciated by those of skill in the art.

DETAILED DESCRIPTION

I. Environment Overview

FIG. 1 is a block diagram of an environment for using a computer system 100 to phase diploid genotypes, according to one embodiment. Depicted in FIG. 1 are an individual 101 (i.e. a human or other organism), a DNA extraction service 102, and a DNA quality control (QC) and matching preparation service 103.

Individuals 101 provide DNA samples for analysis of their genetic data. In one embodiment, an individual uses a sample collection kit to provide a sample, e.g., saliva, from which genetic data can be reliably extracted according to conventional methods. DNA extraction service 102 receives the sample and genotypes the genetic data, for example by extracting the DNA from the sample and identifying values of SNPs present within the DNA. The result is a diploid genotype. DNA QC and matching preparation service 103 assesses data quality of the diploid genotype by checking various attributes such as genotyping call rate, genotyping heterozygosity rate, and agreement between genetic and self-reported gender. System 100 receives the genetic data from DNA extraction service 102 and stores the genetic data in a database 110 containing unphased DNA diploid genotypes (referred to as unphased database 110).

Figure 2A:
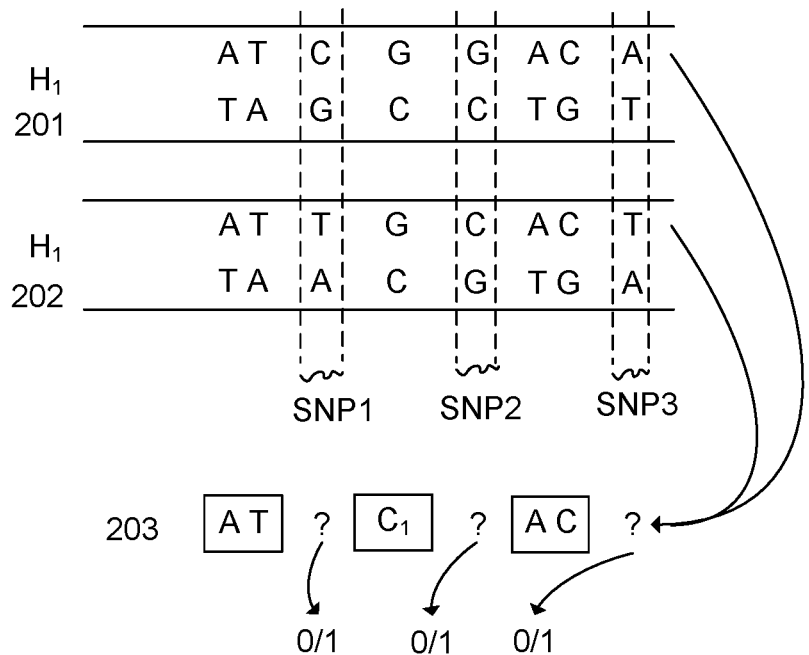
FIG. 2A is a simple illustration of an example pair of phased haplotypes.

FIG. 2A is a simple illustration of an example pair of phased haplotypes. A diploid genotype includes a number of chromosomes and can be phased into two haplotypes, H1 201 and H2 202. In human individuals, one of these haplotypes comes from the individual's mother, the other from the individual's father. Each haplotype contains a sequence of nucleotides, illustrated according to their names, for example ATCGGACA for one strand of H1 201. Single nucleotide polymorphisms (SNPs) are locations within a sequence of nucleotides that differ between individuals of a species. The remaining nucleotides are the same between individuals, and thus are always known. Example 203 illustrates the commonality between sequences in H1 and H2 from the same chromosome and same marker locations within that chromosome. The markers denoted with a "?" are those markers where a SNP is located that indicates a difference in the genetic content between the mother and the father. For sake of simplicity in the following discussion, these are denoted via a bit sequence, with a 1 or a 0 for either the major or minor allele that is possible at that location.

Figure 2B:
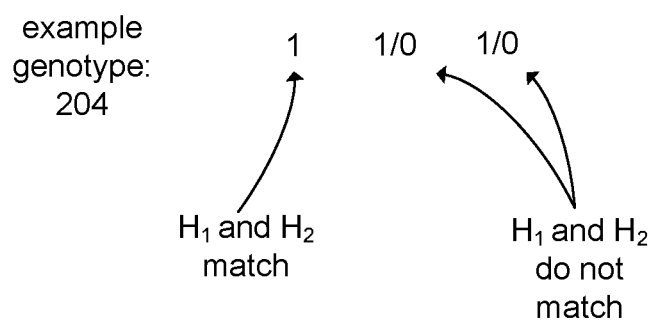
FIG. 2B is a simple illustration of an example diploid genotype.

FIG. 2B is a simple illustration of an example diploid genotype 204. The diploid genotypes received from services 102 and 103 identifies, for each SNP, whether the mother and father of the individual providing a sample have a matching allele value, or whether they have a mismatching allele value. As illustrated in the example diploid genotype 204, a 1 indicates that both the mother and the father have the major value of the allele, a 0 indicates that both the mother and the father have the minor value for the allele, and a 0/1 indicates that there is a mismatch and that one of the mother or the father has the major value of the allele, and that the other has the other value of the allele. This last type of allele value, 0/1, is herein referred to as an unknown allele value.

The challenge of phasing is to identify in input diploid genotypes (where the phasing of the haplotypes has not already been performed) for each unknown allele values which of the mother and the father has which value for the allele. System 100 generally and the phasing module 110 specifically are designed to identify to make these determinations. To accomplish this, the computing system 100 trains and iteratively improves a phasing model trained on both reference DNA samples (reference haplotypes) as well as previously phased input samples that were themselves phased by the phasing model. The phasing model can be initially trained on any reference sample, and updated based on any sample that it phases, meaning that the model can be used to phase any later received input sample without needing to entirely re-train the phasing model.

Figure 3:
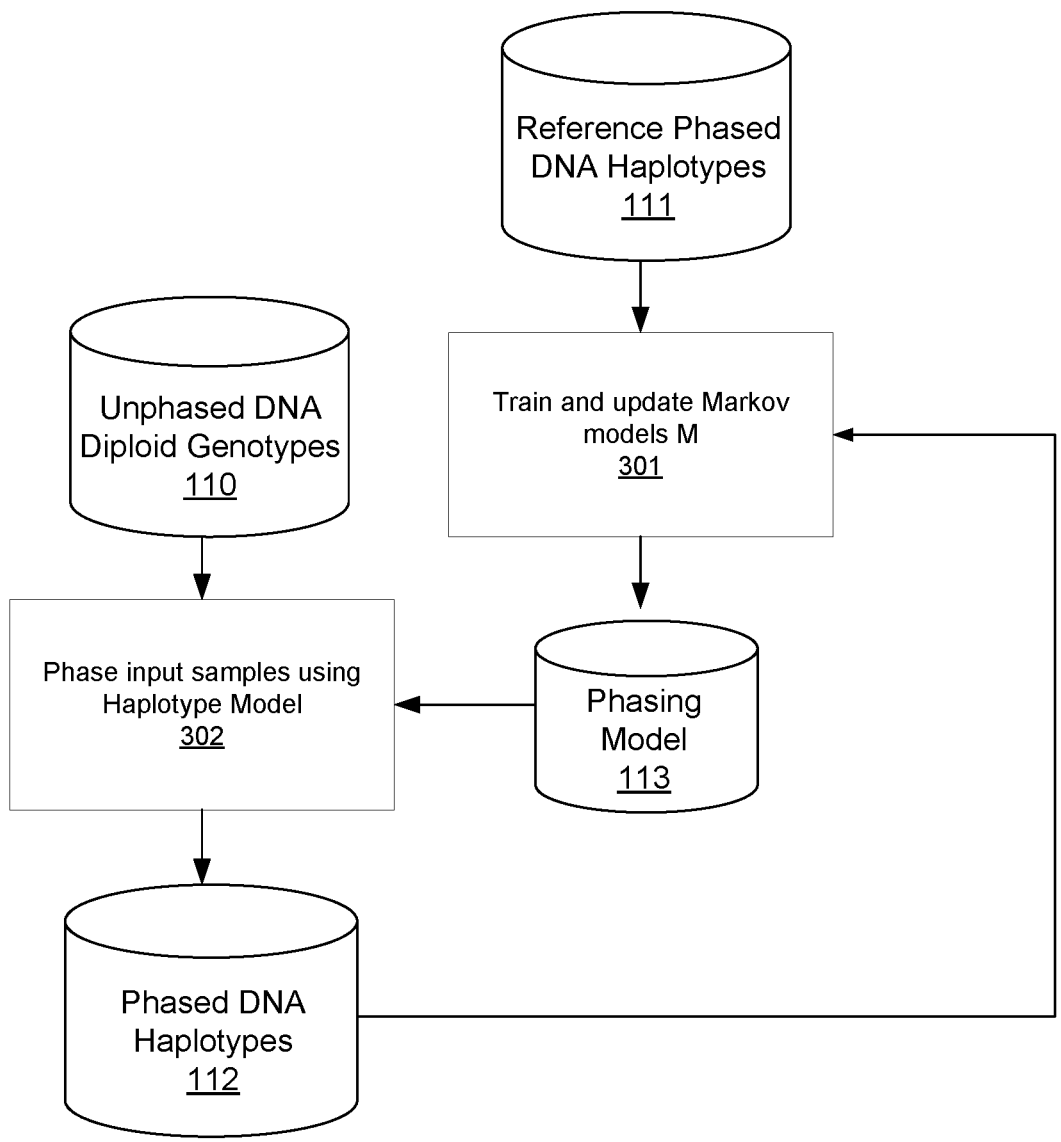
FIG. 3 is a flow diagram for the operation of the computing system for training, updating, and using a phasing model, according to one embodiment.

To perform these operations, the computing system 100 includes a model module 104, a Markov module 105, a merging module 106, a Hidden Markov Model (HMM) module 107, and a phasing module 110. These modules are discussed in relation to FIG. 3, which illustrates a simple flow diagram for one way of using the computing system 100, according to one embodiment.

The model module 104 is responsible for training and updating 301 the Markov models M, which are stored in the phasing model database 113. To accomplish this, the model module 104 calls the Markov module 105 and the merging module 106, and also make uses of reference and already-phased haplotypes stored in in databases 111 and 112. In practice, once any given input diploid genotype sample is phased, the resulting phased haplotypes may be re-used as reference haplotypes for updating the existing Markov models. Training and updating of the Markov models M is further described in Section II, below.

The phasing module 110 performs two major functions 302: 1) updating of the Markov models M to allow for phasing of input samples U, and 2) actually phasing the input samples U once the Markov models M are updated. To perform the first step, the phasing module 110 accesses the Markov models M from database 113 and a set of unphased DNA diploid genotypes U from database 110 and calls the HMM module 107 multiple times to generate, over several iterations, a set of pairs of phased DNA haplotypes that represent a selection of the most probable phased haplotypes for the input diploid genotypes U. The phasing module 110 then provides this set of possible phasings to the Markov model module 105 to update the Markov models M, thereby providing those Markov models M with the ability accurately phase the input samples. This updating processes may be carried out over several iterations to continually improve the ability of the Markov Models M to phase the input samples U. The phasing module 110 then phases the input samples U once more using the updated Markov models M, and returns the result phased haplotypes.

II. Training or Updating Markov Models M for Use in Phasing

To train or update the haplotype model, the model module 104 accesses as input a set of R reference haplotypes from databases 111 and 112. Please note that in this section, "reference haplotypes" may also include previous possible haplotypes for the input samples U from previous use of the phasing module, as introduced above.

Each of the reference phased samples may, for example, be a same chromosome from each of a number of different individuals. The model module 104 provides the R reference haplotypes to the Markov module 105 as input, and the Markov module 105 returns M different haplotype cluster Markov models M (each herein referred to as a Markov model M), each of which is stored in database 113. The M different haplotype models each correspond to a different window of SNPs from the reference haplotypes R, such that each Markov model M is trained on the same window of the chromosome from each of the input samples.

II.a. Input Splitting

Figure 4:
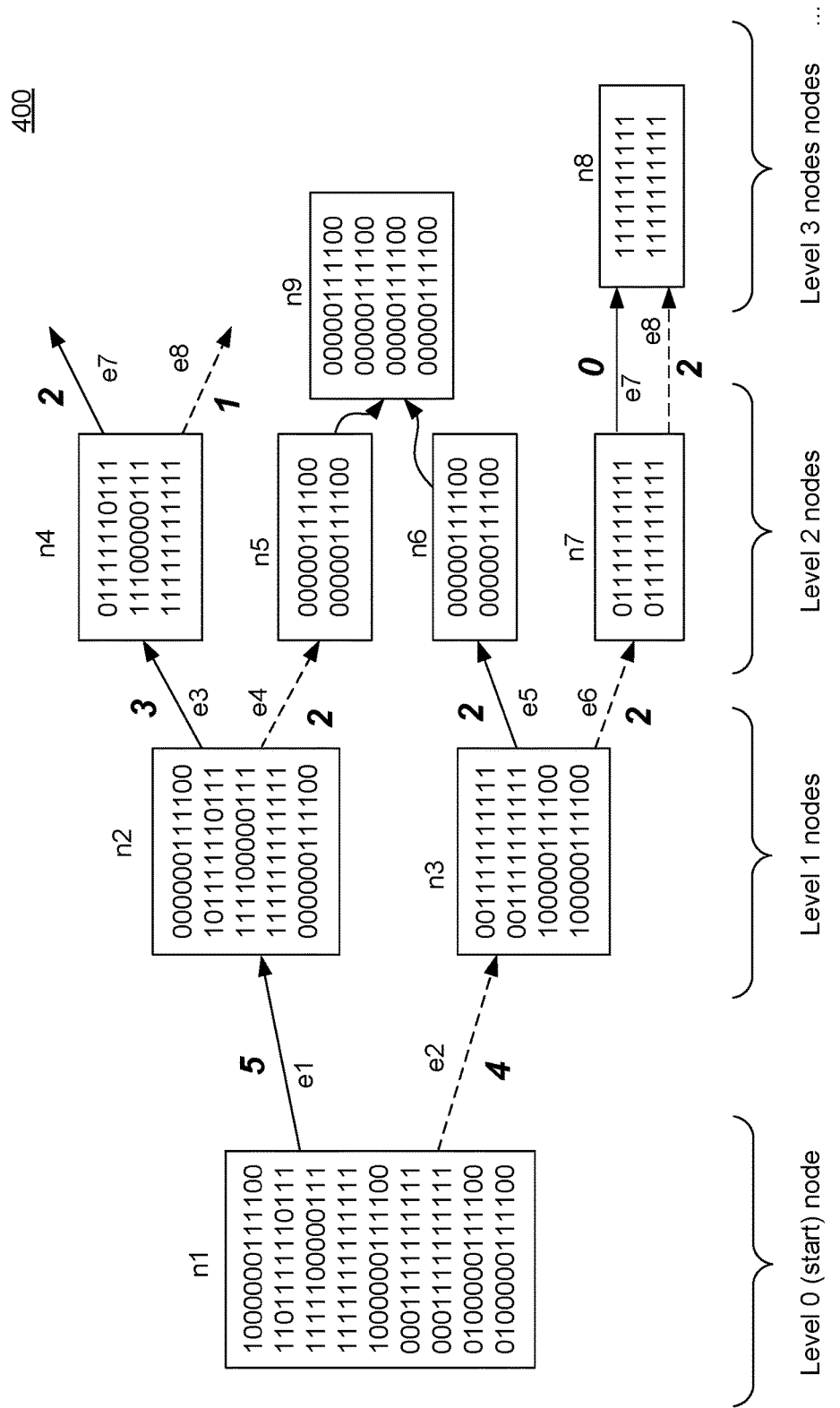
FIG. 4 illustrates an example of the creation of a Markov model M, according to one embodiment.

FIG. 4 illustrates an example of the creation of a Markov model M 400, according to one embodiment. The Markov module 105 generates the Markov model M based on the window of SNPs from each of the reference haplotypes R. Upon completion of the Markov model, each node in the Markov model represents clusters of common haplotypes (sequences of SNPs within the input samples), where all of the haplotypes in each node have the same sequence of SNPs. Each edge between a pair of nodes (i.e., a parent node at level d, and a sub node at level d+1) located at different levels in the Markov model represents one of two possible values for a particular SNP in the haplotypes of the parent node, either the major or minor allele of an allele variant between the haplotypes in a given node (at level d). The edge also represents a transition between the paired nodes (the parent node at one level, and the sub node at the next level).

The Markov module 105 creates the nodes and determines the content of each node of the Markov model by successively splitting the haplotypes in each node into smaller and smaller lengths of SNPs. FIG. 4 provides an exemplary illustration of this process. FIG. 4 illustrates that each node 302 contains a cluster of haplotypes, where individual SNPs are 1s or 0s, where 1 represents the major allele and 0 represents the minor allele. The starting state (node) 202 at level 0 contains all SNPs for that window of all haplotypes from the reference samples. Each node has up to two outgoing edges (or "transitions"), one for the major allele 204a of one of the SNPs in the haplotype and one for the minor allele 204b of that same SNP.

Starting from the starting node's n1 cluster of haplotypes from the reference sample, the Markov module 105 executes a splitting function multiple times that successively splits the haplotypes of each node into pairs of sub nodes generated at the next level in the Markov model. Each split splits the prior node's haplotypes into two haplotype groups. This process is repeated on the sub nodes (now nodes) to generate additional sub nodes at the next level in the model, and so on.

For a given split operation on the haplotypes of a node, one of the two sub nodes includes all haplotypes that have the major allele at a designated SNP index (n2, n4, n6), herein referred to as the splitting index d. The other sub node includes the remaining haplotypes that have the minor allele at the designated SNP index (n3, n5, n7, n8). The Markov module 105 also records the number of haplotypes that were put into each sub node (later referred to as n, for one value of the allele variant and $n_a$ for the alternative value). In FIG. 4, this count appears in bold above next to each edge between nodes. This count is used later by the model module 104 to determine transition probabilities (see Section II.c below). Continuing with the example of FIG. 4, in transitioning from the starting node n1 at level 0 in the Markov model to the sub nodes n2 and n3 at level 1 in Markov model, five haplotypes from the starting node n1 had the major allele 1 at splitting index of d=0 (i.e., the first SNP in each haplotype in the starting node n1), and four haplotypes had the minor allele 0.

The Markov module 105 may also explicitly label the newly created sub nodes as having a level d where d is the number of parent nodes to the sub nodes, which is equivalent to the number of prior splits that have been performed to arrive at those sub nodes.

Example pseudocode for performing the split is as follows:

```
level s_0 ← node (haplotypes = X, parents = Ø)
for each level d in [1,2,...,D] do
    level s_d ← Ø
    for each node x in level s_{d-1} do
        S ← SPLIT (x.haplotypes, d) / / (split up node's haplotypes
            by allele d)
        x.children_0 ← node(haplotypes = S_0, parents = {x})
        x.children_1 ← node(haplotypes = S_1, parents = {x})
```

In one embodiment, the splitting function itself takes as input a set of reference haplotypes X where each haplotype includes a number of sequential SNPs, each SNP having an index, and a splitting index. The splitting function outputs two subsets of haplotypes (the contents of the sub nodes) each including a number of sequential SNPs that is one less than the number of SNPs from the parent. The first subset includes all haplotypes where allele at splitting index is the major allele, and second subset includes all haplotypes where the allele at the splitting index is the minor allele.

In one embodiment, the SNP located at the splitting index is omitted from the SNPs in the haplotypes in the sub nodes, however this is not strictly necessary. These omitted SNPs are allele variants, and are instead represented by the edges between the nodes of the Markov model.

Example pseudocode for implementing the splitting function is as follows:

```
procedure split (X,d)
    S_0 ← Ø
    S_1 ← Ø
    for each haplotype h in X do
        if h_d = 0 then / / if the allele at position d is zero...
            S_0 ← S_0 ∪{h} / / add h to S_0
        else
            S_1 ← S_1 ∪{h}
    return S/ / where S is {S_0 ← S_1}
```

In one implementation, when calling the splitting function the Markov module 105 selects the splitting index to be the first SNP in any of the reference haplotypes in a given node where one of the alleles varies from another allele in one of the other haplotypes in the group.

II.b. Merging Similar Sub Nodes

After splitting of the nodes at a given (prior) level, the Markov module 105 merges all sub nodes at the new/next level where the reference haplotypes in those sub nodes are determined to be sufficiently to each other. These sub nodes are merged into a single sub node located at the same level in the model and containing all of the haplotypes of the merged sub nodes. Merging is performed to reduce the size and bias of each Markov models by consolidating clusters of similar reference haplotypes from disparate markers within the reference sample.

Continuing with the example of FIG. 4, nodes n5 and n6 are at the same level 2 and include similar (in this example identical) haplotypes. As such, they would be merged into a single node n9 located at level 2 containing all of the haplotypes of both nodes n5 and n6.

To accomplish merging, the model module 104 calls a merging module 106 which determines whether to merge one or more nodes at a given level. The merging module 106 keeps two nodes X and Y as separate nodes in the model if there exists a reference haplotype h of any length that is determined to be sufficiently likely to belong to one of nodes X or Y but not the other (i.e., P(h|X)≠P(h|Y)). To make this determination, the merging module 106 determines $n_x$ and $n_y$, the number of haplotypes in nodes X and Y, respectively. The merging module 106 also determines $n_x(h)$ and $n_y(h)$, the number (frequency) of occurrences of haplotype h in nodes X and Y, respectively.

Depending upon the embodiment, the merging module 106 further determines different sets of intermediate quantities. In some embodiments, the merging module 106 also determines the relative frequency of haplotype h in nodes X and Y relative to other haplotypes $$\left(i.e., \widehat{p_x}^{(h)} = \frac{n_x(h)}{n_x}, \widehat{p_y}^{(h)} = \frac{n_y(h)}{n_y}\right).$$

In these embodiments, the determination of whether to merge nodes X and Y is made based on these relative frequencies.

In other embodiments, rather than relying on the relative frequencies of appearance of the haplotypes in nodes X and Y alone, the merging module 106 instead models the probability of haplotype h appearing in nodes X and Y with $$\widehat{p_x}^{(h)} = \frac{n_x(h) + \alpha}{n_{x+\alpha+\beta}} \text{ and } \widehat{p_y}^{(h)} = \frac{n_y(h) + \alpha}{n_{y+\alpha+\beta}}.$$

In these embodiments, the determination of whether to merge nodes X and Y is made according to:

$$\left|\widehat{p_x}^{(h)} - \widehat{p_y}^{(h)}\right| \geq C^2 \sqrt{\frac{\widehat{p_x}^{(h)}\left(1 - \widehat{p_x}^{(h)}\right)}{n_x} + \frac{\widehat{p_y}^{(h)}\left(1 - \widehat{p_y}^{(h)}\right)}{n_x}} \quad (1)$$

where C is a function of the p-value to be applied, and is chosen to optimize model size, which in turn influences phasing speed and accuracy. Generally, smaller values for C result in larger model sizes that will be more accurate but will slow phasing speed, and larger values for C will result in smaller model sizes will be less accurate but will improve phasing speed. In one embodiment α and β are chosen to be 0.5, but this may vary.

In this embodiment, if the merging module 106 determines that the magnitude of the difference between the probabilities for nodes X and Y a given haplotype h is greater than the other side of equation 1, then the merging module 106 determines that it is sufficiently likely that haplotype h will appear in node X or Y but not the other. If this occurs, merging module 106 will not merge nodes X and Y.

Example pseudocode for equation 1 for merging nodes at level d in a model that has D levels is as follows:

```
procedure COMPARE(X,n_x,Y,x_y,d,D)
if d > D then
    return (similar = TRUE, score = 0) // no more alleles to compare
S_x ← SPLIT(X,d) // split X according to the allele at SNP d
S_y ← SPLIT(Y,d) // also Y
// First, see if Sx_0 and Sy_0 are different
px_0 ← (|Sx_0| + α)/(n_x + α + β)
py_0 ← (|Sy_0| + α)/(n_y + α + β)
score_0 ← ((px_0 − py_0) · (px_0 − py_0))/((px_0 · (1 − px_0))/n_x + (py_0 · (1 − py_0))/n_y)
if score_0 ≥ C then
    return (similar = FALSE, score = N/A)
// Now try comparing haplotypes with a "1" at allele d
px_1 ← (|Sx_1| + α)/(n_x + α + β)
py_1 ← (|Sy_1| + α)/(n_y + α + β)
score_1 ← ((px_1 − py_1) · (px_1 − py_1))/((px_1 · (1 − px_1))/n_x + (py_1 · (1 − py_1))/n_y)
if score_1 ≥ C then
    return (similar = FALSE, score = N/A)
// Compute the highest score we could get in the recursion that follows
lowpx_0 ← α)/(n_x + α + β)
lowpy_0 ← α)/(n_z + α + β)

maxscore_0 ← max( (lowpx0 − py0) · (lowpx0 − py0) / ((lowpx0 · 1(1 − lowpx0))/nx + (py0 · (1 − py0))/ny), (lowpx0 − py0) · (lowpx0 − py0) / ((lowpx0 · 1(1 − lowpx0))/nx + (py0 · (1 − py0))/ny) )

// Continue only if enough haplotypes remain for test to find different distributions
if maxscore_0 ≥ C then
    score_0 ← max(score_0,COMPARE(Sx_0,n_x,Sy_0,n_y,d + 1,D))
    if score_0 ≥ C then
        return (similar = FALSE, score = N/A)
lowx_1 ← α)/(n_x + α + β)
lowy_1 ← α)/(n_z + α + β)

maxscore_0 ← max( (lowpx1 − py1) · (lowpx1 − py1) / ((lowpx1 · 1(1 − lowpx0))/nx + (py1 · (1 − py0))/ny), (px1 − lowpy1) · (pz1 − lowpy1) / (px1 · (1 − pz1))/nx + (lowpy1 · (1 − lowpy1))/ny) )

if maxscore_1 ≥ C then
    score_1 ← max(score_0,COMPARE(Sx_1,n_x,Sy_1,n_y,d + 1,D))
    if score_1 ≥ C then
        return (similar = FALSE, score = N/A)
// Finally, we can say the distributions are close enough to merge two nodes
return (similar = TRUE, score = max (score_0, score_1))
```

Merging using equation 1 rather than relative frequencies of occurrence has numerous benefits over existing methods of merging nodes of haplotypes in a Markov model. Relative to a merging equation that uses relative frequencies and simply a constant such as C rather than adding any other terms (see D. Ron, Y. Singer, and N. Tishby. On the learnability and usage of acyclic probabilistic finite automata. *J. Comp Syst. Sci.*, 56:133-152, 1998), equation 1 is not as likely to observe a large difference in haplotype frequencies if $n_x$ or $n_y$ is small. This makes equation 1 merge more consistently for different values of $n_x$ and $n_y$. Relative to a merging equation that uses relative frequencies and includes a term that depends on $n_x$ and $n_y$, (see Sharon R. Browning. Multilocus associate mapping using variable-length Markov chains. *American Journal of Human Genetics*, 78:903-913, 2006), equation 1 also accounts for the proportions of the haplotypes in X and Y themselves $n_x(h)$ and $n_y(h)$, and not just $n_x$ and $n_y$. This makes equation 1 merge more consistently for different proportions of $n_x(h)$ and $n_y(h)$ as well as for different values of $n_x$ and $n_y$. Finally, relative to a merging equation that uses relative frequencies instead of the modeled probabilities $\widehat{p_x}^{(h)}$ and $\widehat{p_y}^{(h)}$ but is otherwise similar to equation 1, equation 1 do not have the drawback of creating a result that is too confident in its estimation of variance when the relative frequency of occurrence of a haplotype is close to 0 or 1. The modeled probabilities $\widehat{p_x}^{(h)}$ and $\widehat{p_y}^{(h)}$, being regularized using for example a symmetric beta distribution as introduced above, do not have this drawback.

Merging module 106 repeats this process for all of nodes X and Y under consideration, comparing each node against every other node for possible merging, until all nodes have been checked, and all nodes that are sufficiently similar according to equation 1 have been merged with each other.

II.c. Markov Model Completion and Edge Probability Assignment

After a sufficient number of splits, terminating (leaf) nodes in the Markov model M will contain reference haplotypes where all the SNPs in these nodes have the same allele (major or minor) at every index in the haplotype. Thus, in these nodes all of the haplotypes in each node are identical, and the count of the number of haplotypes in each node may be separately stored in the model.

Each edge of the Markov model (labeled in FIG. 4 as edges e1-e8) is assigned a transition probability that is based on the allele counts associated with the outgoing node (rather than the incoming sub node on the other side of the edge). The transition probability for allele variant a of the model is set according to:

$$P(a) = \frac{\gamma}{2} + \frac{n_a}{n_a + n_{\bar{a}}}(1 - \gamma) \quad (2)$$

where $n_a$ is the count of haplotypes having allele a for that edge/node-sub node combination, and $n_{\bar{a}}$ is the count of haplotypes having the alternative allele. Here, $\gamma$ is a system-specified probability. In one embodiment, it is selected to be the likelihood of a genotype error, in which case either allele is equally likely and is therefore 0.5, however it may vary in other embodiments.

A consequence of using equation 2 to assign transition probabilities to edges is that any edge and associated sub node with a haplotype count of zero for a given value for an allele variant is assigned a nonzero transition probability (i.e., $$\frac{\gamma}{2}$$

if equation 2 is used) despite not having any such haplotypes in the sub node. Further, in this case the Markov module 105 assigns/connects the other edge with the zero haplotype count to the same sub-node as the alternative value for the allele. This is illustrated in the example of FIG. 4, where allele value of X has zero associated haplotypes in node n7, and thus the sub node associated with that allele value is empty (not shown). As a result, the edge e7 for that allele value (1) is connected to the sub node n8 for the alternate allele value (0).

A benefit of assigning transition probabilities in this manner where they would not otherwise exist based on haplotype counts is that as a result, the Markov model is able to represent likelihoods for all possible haplotypes. As a result, corresponding diploid HMMs that are created based on the Markov model (described further below in section III) can phase any genotype, even new genotypes that contain haplotypes that do not appear in the reference sample used to generate the Markov model. As a result, new Markov models do not need to be trained each time a new DNA sample needs to be phased.

The output of the Markov module 105 is a Markov model X having d+1 levels, where each set of nodes in the model transitions to nodes in the next level. The transitions between nodes (i.e., the model's edges) are the allele variants that were used to split the nodes to create the levels of the Markov model. The Markov model represents a probability distribution over the reference haplotypes in each node.

Example pseudocode for the overall creation of the model (including the windowing portion as previously reproduced above) is as follows:

```
procedure MODEL(X)
    levels₀ ← node(haplotypes = X, parents = Ø)
    for each level d in [1,2,...,D] do
        levels_d ← Ø
        for each node x in levels_{d-1} do
            S ← SPLIT(x.haplotypes, d) // (split up node's haplotypes by
            allele d, see procedure COMPARE)
            x.children₀ ← node(haplotypes = S₀, parents = {x})
            x.children₁ ← node(haplotypes = S₁, parents = {x})
        Q ← Ø // initialize [priority] queue to empty
        for each pair of nodes x,y in levels_d do
            similar, score ← COMPARE(x.haplotypes, y.haplotypes,
            | x.haplotypes |, | y.haplotypes |, d,D)
            if similar then
                enqueue(Q,r,y,score) // enqueue pair x,y
        while Q is not empty do
            x,y, score ← pop(Q)// get most similar nodes x,y
            if x and y are still in levels_d then
                levels_d ← levels_d \ [x,y] // remove x and y from level d
                // and merge nodes x and y:
                z ← node(haplotypes = x.haplotypes ∪ y.haplotypes, parents =
                x.parents ∪ y.parents)
                for each node p in x.parents do
                    replace x and y with z in p.children
                for each node w in levels_d do
                    similar, score ←
                    COMPARE(z.haplotypes,w.haplotypes, | z.haplotypes |,
                    | w.haplotypes |, d, D)
                    if similar then
                        enqueue(Qz,w,score)
                levels_d ← levels_d ∪ {z}// finally, add z to level d
    return levels/ / return model
```

II.d. Inter-Markov Model Accuracy

As introduced above, the model module 104 provides as input a number of different windows of SNPs to the Markov module 105 to produce the resulting Markov modules M. Selection of the windows affects the accuracy of the resulting phasing model which uses the Markov models. When a larger reference sample, such as a reference chromosome, is divided up into windows and turned into Markov models, the first and last few SNPs in each Markov model may be less accurate, because these SNPs have shorter upstream or downstream haplotypes from which to learn.

The model module 104 may address this problem by choosing the windows of the chromosome to be phased so that the windows of SNPs partially overlap. In practice, this means that at least some of each Markov model M overlaps with the adjacent windows of SNPs and their corresponding Markov models M−1 and M+1. In one embodiment, this overlap is approximately 100 SNPs, where the windows passed in to module 105 to generate the Markov models are approximately 500 SNPs long. In one embodiment, the exact length of SNPs used in a window is selected so that the middle of the overlap between two windows to be used is located a marker that is approximately at the mid-point of the overlap between the two windows (e.g., approximately 50 SNPs) that is also an allele variant between the two referenced phased haplotypes that are passed in to module 105 in both of the overlapping windows. By doing this, the model module 104 ensures that phasing decisions made near one of the extreme ends of any Markov model are not part of the phased result of the model.

FIG. 7A illustrates an example of overlapping adjacent windows of SNPs used to generate Markov models M, according to one embodiment. Brackets illustrate how the windows used to generate Markov models may overlap, for example for Markov models 7 and 8.

III. Using the Markov Model to Phase Diploid Genotypes

Once the Markov models have been generated by the Markov module 105, the model module 105 calls the phasing module 110, which takes as input the Markov Models M and a set of U unphased DNA diploid genotypes to be phased. Section III.a describes the updating of the of the Markov Models M to account for the input samples U to be phased. Section III.b describes how the updated Markov Models M are used to identify the most probable phasing for each of the samples u in the set U. Section III.c walks through an example phasing of an input diploid genotype sample u, which is performed as part of the model updating in Section III.a and the output phasing in Section III.b.

Example pseudocode for the updating of the Markov Models M and the phasing the set of U samples by the phasing module 110 is as follows, where M in the pseudocode includes the entire set of Markov models M, one Markov model M for each of the windows of the chromosome to be phased:

```
procedure PHASE (R,U)
  //Phase each sample in U randomly R times each and call the result P
  for iteration i in [1,2,....,MAX-ITERATIONS] do
    M ← MODEL (R ∪ P) // Learn haplotype cluster Markov model
    P ← ∅
    for u ∈ U do
      if i = MAX-ITERATIONS then
        // For the last iteration, set the final phase of u from the
        Viterbi path in the diploid-HMM
        P ← P ∪ DIPLOID-HMM-VITERBI(M, u)
      else
        // Sample R possible ways of phasing u from M
        for i in [1,2,....,R] do
          P ← P ∪ DIPLOID-HMM-SAMPLE(M, u)
  return P
```

III.a. Updating the Phasing Model.

The phasing module 110 calls the HMM module 107 a number of times to phase each of the input samples u in the set U into a set of pairs of haplotypes for each window. The pairs of phased haplotypes in the set represent a subset of the most probable phasings for input sample u. The mechanism for selecting the subset may vary by implementation. For example, the set of pairs of phased haplotypes may be randomly selected from the top 20 most probable phasings.

After each iteration of phasing the set of input samples U, the phasing module 110 calls the Markov module 105 to regenerate or update the Markov Models M to include the sets of pairs of phased haplotypes identified for each of the samples u in the set of samples U. For sake of example, assume there were 200 pairs of haplotypes in the reference set of haplotypes used to originally generate the Markov Models M, and that there are 10 input samples in the set U. Further assume that after each iteration of phasing of the set of input samples U, four pairs of phased haplotypes were selected for each sample u in the set U. Consequently, in this example after the first iteration of phasing using the HMM module 107, 40 pairs of phased haplotypes that represent probable (but not necessarily the most likely) phasing for the input samples are identified. The phasing module 110 then calls the Markov module 105 to add these 40 pairs of phased haplotypes to the original reference set of 200, so that the Markov Models will be regenerated or updated based on 240 haplotypes instead of 200.

The phasing module 110 again calls the HMM module 107 to phase the input samples U again, each time using the updated Markov models M that incorporate the phased haplotypes generated from the previous iteration's phasing. Updating the Markov Models M will affect the nodes of the Markov models M as well as the transition probabilities. The consequence of this is that on the next iteration of phasing performed by the HMM module 107, the resulting probabilities for various phasings will very likely be different than on the previous iteration.

As above, this process is repeated a number of times (i.e., MAX-ITERATIONS-1, where MAX-ITERATIONS is any integer). Each time, the selected probable phasings used to regenerate or update to the Markov Models M, and the phasings of the input samples U are re-done.

III.b. Phasing Samples Using the Phasing Model

To phase the set of input samples U, the phasing module 110 again calls the HMM module 107 once for each input sample u and each Markov module M, which corresponds to one call for each window of the chromosome to be phased. In contrast to the process for updating the Markov Models as described in Section III.a above, rather than picking a set of pairs of possible phased haplotypes for each window, the phasing module 110 obtains a single pair of possible phased haplotypes that represent the most probable phasing of the input sample u for that window. The phasing module 110 may aggregate these results, thereby identifying, for a given input sample u, a set of pairs of possible haplotype phasings, one pair for each of the windows in the input chromosome to be phased.

For a given input sample u, the set of pairs of haplotypes needs to be joined across all windows to generate a single pair of haplotypes. The overlap in SNPs for adjacent discussed with respect to FIG. 7A above is useful for joining the haplotype pairs across windows. FIG. 7B illustrates an example of how overlapping windows of phased haplotypes can be used to join the haplotypes across windows.

In one embodiment, given two pairs of phased haplotypes from adjacent windows, a heterozygous SNP near the middle of the overlap of the two windows is selected for each pair. To determine whether to attach a first haplotype H1 of a first pair P1 to a first H3 or a second H4 haplotype of a second pair, determination is made as to whether the selected allele of the first haplotype H1 matches the first H3 or the second H4 haplotype of the second pair. If the selected allele of the first haplotype H1 of the first pair matches the corresponding allele of the first haplotype H3 of the second pair, then the first haplotypes of both pairs H1 and H3 are concatenated together, removing any alleles in the overlap between the two windows. A similar operation is performed on the second haplotypes H2 and H4 in the pair.

On the other hand, if the selected allele of the first haplotype H1 of the first pair does not match the corresponding allele of the first haplotype H3 of the second pair (or, alternatively, does match the corresponding allele of the second haplotype H4 of the second pair), then the first haplotype H1 of the first pair is concatenated with the second haplotype H4 of the second pair, again removing any alleles in the overlap between the two windows. Again, a similar operation is performed for the remaining haplotypes H2 and H3 from each pair.

In alternate embodiments, more than one SNP in the overlap may be used to determine which of the haplotypes of each pair match up with each other. For example, if two or more SNPs in the overlap generate conflicting answers regarding which of the haplotypes of each pair should be concatenated together, the number of SNPs favoring each conclusion may be used to determine a probability that one matchup versus another is the correct one.

This process repeats for all windows of the chromosome. Once the pairs of haplotypes are concatenated, the phasing module then returns the pair of phased haplotypes for each input sample u in the set U.

III.c. Phasing a Single Input Sample u for a Single Markov Model M

Each individual's u diploid genotype is separately phased by the HMM module 107, where the HMM module 107 phases each window of a diploid genotype u with the Markov model trained for that same window. An example of a portion of an example diploid genotype $u_M$ for a single individual corresponding to a given Markov model M may be labeled as follows, in accordance with the example genotype illustrated in FIG. 2: $u_M$=(1, 1/0, 1/0). In practice, the length in SNPs of $u_M$ will be the same as the length in SNPs of the window used to train the Markov model M.

The HMM module 107 walks through the Markov model M, from node 0 at level 0 level by level, where at each edge, the HMM module 107 calculates the conditional probability of transitioning to one of the sub-nodes of the current node, given the input diploid genotype. This provides a possible phasing for the haplotypes of the mother and father, determined on a node by node basis, herein referred to as (mother, father), where each of mother and father is a vector of possible phased allele values such as 101, 111, 100, etc.

This means that at each node, at SNP i where the mother and father match (i.e., where $u_M$ (i) is known to be a 1 or a 0), the conditional probability is the product of the probability to arrive at a given node for both the mother and father given the genotype preceding i multiplied by the probability of selecting the allele value that corresponds to the known allele value in the diploid genotype (i.e., 0 or 1). However, for an unknown allele value at SNP i where the mother and father do not match (i.e., where it is unclear whether $u_M$ (i) is 1 or 0, denoted 1/0), two conditional probabilities must be calculated, where each is the product of the probability to arrive at a given node for both the mother and the father given the genotype preceding i multiplied by, for the first conditional probability, the probability of picking allele value 1 for the mother and 0 for the father, and, for the second conditional probability, the probability of picking allele value 0 for the mother and 1 for the father.

Figure 5:
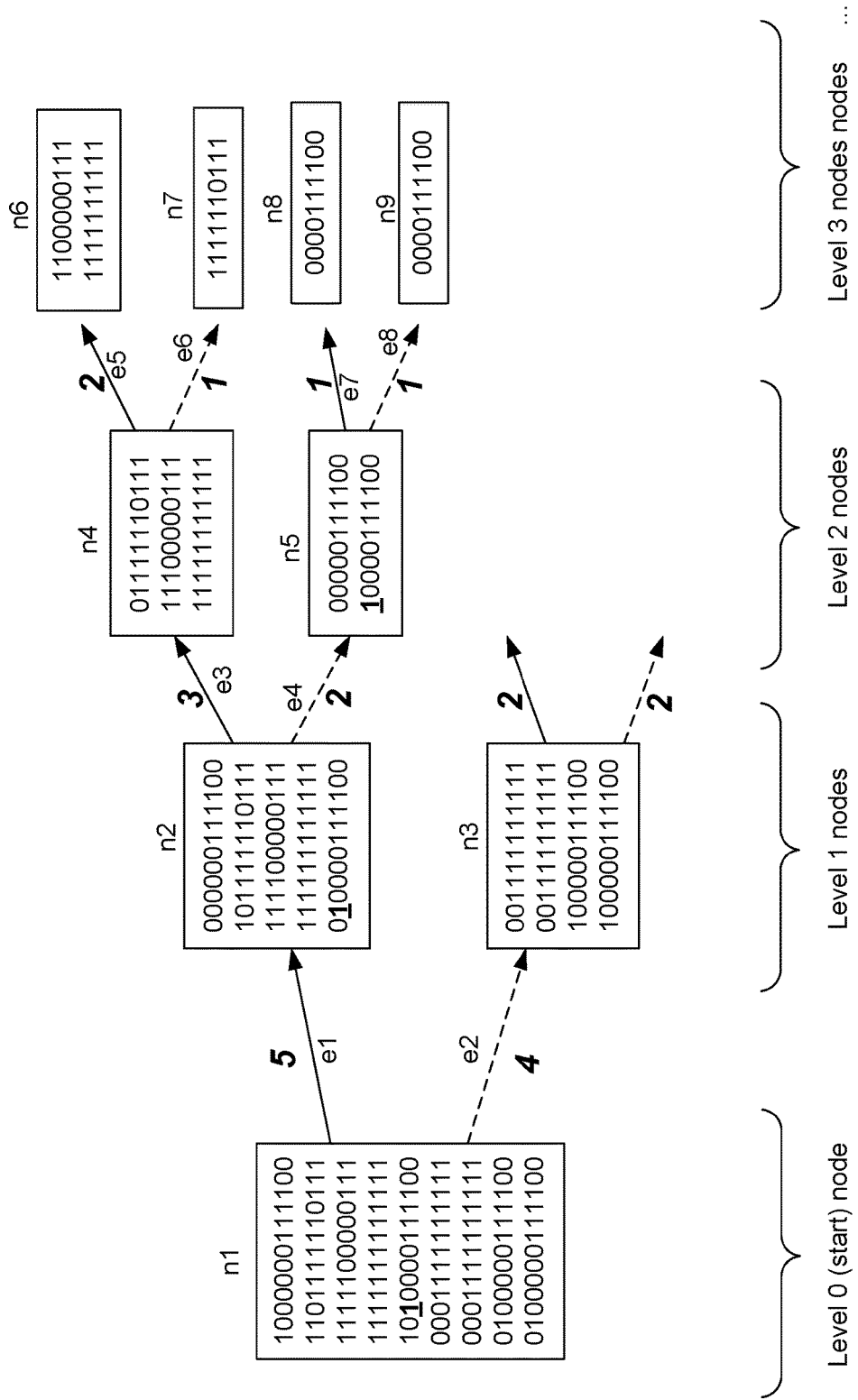
FIG. 5 is a slightly modified version of the Markov Model from FIG. 4 for use in explaining the phasing of a window of a diploid genotype, according to one embodiment.

As an example, consider the example genotype $u_M$ above in accordance with the example Markov model from FIG. 5. The example Markov model in FIG. 5 is similar to the example Markov model from FIG. 4, except one SNP (bolded and underlined) has been adjusted to better illustrate the growth of the number of possible phasings based on diploid genotypes, and only those edges relating to this specific example have been labeled. For clarity of description, the conditional probabilities calculated below with respect to the example Markov model of FIG. 5 use simplified equation (3A) rather than the more complete equation (2).

The conditional probability of the SNP at index i=1 being the major value for both the mother and the father is based on the counts of haplotypes associated with each edge e1 and e2 and each sub node n2 and n3 as provided by the Markov model M. This may be illustrated as follows:

$$P((\text{mother, father})|\{\text{edges}\}) = \frac{\gamma}{2} + \frac{n_a}{n_a + n_{\bar{a}}}(1-\gamma) \cong \frac{n_a}{n_a + n_{\bar{a}}} \quad (3A)$$

$$P((1, 1)|\{e1, e2\} \times \{e1, e2\}) \cong \frac{n_{n2}}{n_{n2} + n_{n3}} \cdot \frac{n_{n2}}{n_{n2} + n_{n3}} \quad (3B)$$

$$P((1, 1)|\{e1, e2\} \times \{e1, e2\}) \cong \frac{5}{9} \cdot \frac{5}{9} = \frac{25}{49} \quad (3C)$$

where the multiplication of the two different probabilities accounts for both the probability of the mother's haplotype to arrive at a given node and also the probability of the father's haplotype to arrive at a given node. Only one conditional probability is calculated because the SNP at i=1 for the mother and father matches.

At SNP i=2, however, two conditional probabilities are calculated based on the possible different phasings of the diploid genotypes. These are as follows, based on the counts of haplotypes associated with each edge e3 and e4 and each sub node n4 and n5 as provided by the Markov model M:

$$P((10, 11)|\{e1, e2, e3, e4\} \times \{e1, e2, e3, e4\}) \cong \quad (4A)$$

$$\left(\frac{n_{n2}}{n_{n2}+n_{n3}} \cdot \frac{n_{n5}}{n_{n4}+n_{n5}}\right) \cdot \left(\frac{n_{n2}}{n_{n2}+n_{n3}} \cdot \frac{n_{n4}}{n_{n4}+n_{n5}}\right)$$

$$P((10, 11)|\{e\} \times \{e\},) \cong \left(\frac{5}{9} \cdot \frac{3}{5}\right)\left(\frac{5}{9} \cdot \frac{2}{5}\right) = \frac{2}{27} \quad (4B)$$

and separately $$P((11, 10)|\{e1, e2, e3, e4\} \times \{e1, e2, e3, e4\}) \cong \quad (5A)$$

$$\left(\frac{n_{n2}}{n_{n2}+n_{n3}} \cdot \frac{n_{n4}}{n_{n4}+n_{n5}}\right) \cdot \left(\frac{n_{n2}}{n_{n2}+n_{n3}} \cdot \frac{n_{n5}}{n_{n4}+n_{n5}}\right)$$

$$P((11, 10)|\{e\} \times \{e\},) \cong \left(\frac{5}{9} \cdot \frac{2}{5}\right)\left(\frac{5}{9} \cdot \frac{3}{5}\right) = \frac{2}{27} \quad (5C)$$

Although the probabilities of these possible alternate phasings (i.e., (10, 11) and (11, 10) are the same, SNP i=3 illustrates how the probabilities of different phasings will various as more variant alleles are encountered in the window to be phased. Continuing with the example of $u_M$ at SNP i=3 in this example further illustrates how additional conditional probabilities are calculated based on further possible alternate phasings within the diploid genotype. Some of the possible phasings will be based on the counts of haplotypes associated with edges e5 and e6 and sub nodes n6 and n7. However, other possible phasings will be based on the counts of haplotypes associated with edges e7 and e8 and sub nodes n8 and n9.

$$P((101, 110)|\{e\} \times \{e\} \times \{e\}) \cong \frac{2}{27} \cdot \left(\frac{n_{n8}}{n_{n8}+n_{n9}} \cdot \frac{n_{n9}}{n_{n8}+n_{n9}}\right) = \quad (6)$$

$$\frac{2}{27} \cdot \left(\frac{1}{2} \cdot \frac{1}{2}\right) = \frac{1}{54}$$

$$P((100, 111)|\{e\} \times \{e\} \times \{e\}) \cong \frac{2}{27} \cdot \left(\frac{n_{n9}}{n_{n8}+n_{n9}} \cdot \frac{n_{n8}}{n_{n8}+n_{n9}}\right) = \quad (7)$$

$$\frac{2}{27} \cdot \left(\frac{1}{2} \cdot \frac{1}{2}\right) = \frac{1}{54}$$

$$P((111, 100)|\{e\} \times \{e\} \times \{e\}) \cong \frac{2}{27} \cdot \left(\frac{n_{n6}}{n_{n6}+n_{n7}} \cdot \frac{n_{n7}}{n_{n6}+n_{n7}}\right) = \quad (8)$$

-continued $$P(\{110, 101\}|\{e\} \times \{e\} \times \{e\}) \cong \frac{2}{27} \cdot \left(\frac{n_{n7}}{n_{n6} + n_{n7}} \cdot \frac{n_{n6}}{n_{n6} + 7}\right) = \quad (9)$$

$$\frac{2}{27} \cdot \left(\frac{2}{3} \cdot \frac{1}{3}\right) = \frac{4}{243}$$

$$\frac{2}{27} \cdot \left(\frac{1}{3} \cdot \frac{2}{3}\right) = \frac{4}{243}$$

Although the growth of the number of possible phasings created by iterating through the Markov model SNP by SNP in the diploid genotype is less than quadratic (as some SNPs are shared by the mother and father as above), even within a window of 500 SNPs the number of possible phasings will grow incredibly quickly. Further, the HMM module 107 generates many such sets of possible phasings, one for each Markov model and corresponding window of the input chromosome to be phased, and for each input sample u in the set U. The end result is that from a computer processing time/processor and memory perspective, maintaining every possible alternate phasing for an arbitrary sample $u_M$/Markov model M combination can be prohibitively costly from both a computer processing time perspective and a computer memory storage perspective.

The HMM module 107 addresses this potential problem by deleting alternate phasings that have below a threshold level of probability μ, or by deleting a sufficient number of alternate phasings such that a threshold amount of the total probability (for all possible phasings) ε has been deleted, or by calculating the probability of those phasings that represent a threshold amount of the total probability for all possible paths (1−ε). For example, after determining the possible phasings after each SNP index i, the HMM module 107 deletes possible phasings, starting from the total probably of deleted possible phasings is the threshold ε. The HMM module 107 then proceeds to determine the possible phasings for SNP index i+1, and then again deletes possible phasings until the threshold ε is again reached.

The process described above is repeated for each SNP index i in the window to be phased. Each possible phasing may be described as a Hidden Markov Model (hence the name of the module), where each state in the HMM/possible phasing represents an ordered pair of states in the Markov M, one for each haplotype in the diploid genotype.

Figure 6:
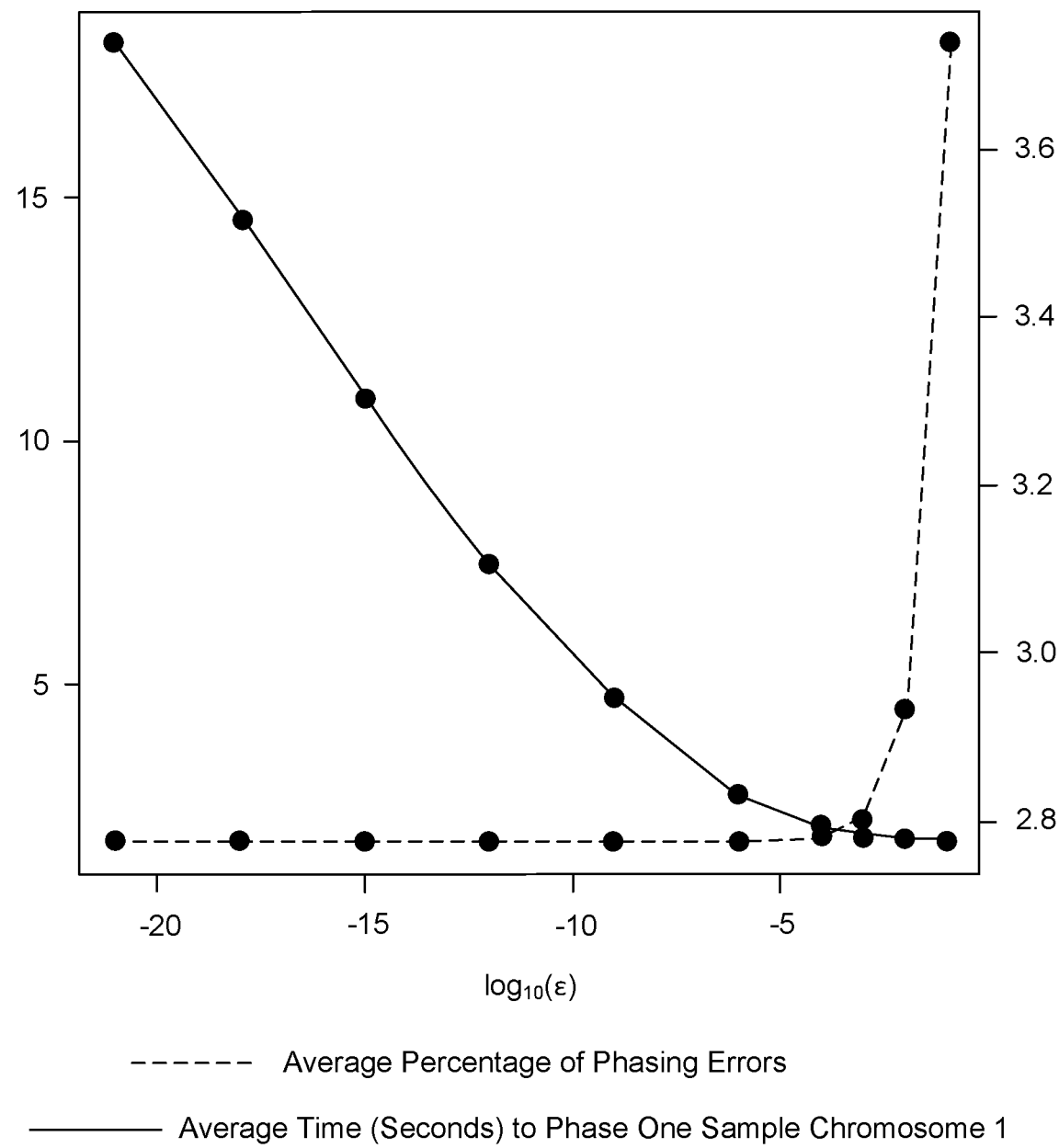
FIG. 6 is a graph showing the phasing time required to phase human chromosome 1 of an input DNA diploid genotypes for various values of a threshold ε, according to one embodiment.

FIG. 6 is a graph showing the phasing time required to phase human chromosome 1 of an input DNA diploid genotypes for various values of a threshold ε, according to one embodiment. Using the processes described herein, if ε is set to zero, the average sample phasing time is 100.2 seconds, and the average phasing error rate is 2.77%. Increasing ε to be in a range between 0 and ε $10^{-6}$ does not measurably change the error rate (2.77%), but decreases the phasing time linearly to approximately 5 seconds at ε≅$10^{-6}$, which is a twenty fold improvement in phasing time vs. an implementation that does not delete possible alternate phasings. At thresholds ε≥$10^{-6}$, the average phasing error rate increases appreciably with no appreciable decrease in phasing size. For sake of completeness, the phasing times reported in this paragraph do not include file input/output (read/write) or recombining phased segments together. In one embodiment, ε is set at $10^{-15}$, which means that 99.9999999999999% of the total probability for possible phasings is kept at each level of the HMM, which reduces the phasing search space (i.e., the number of possible phasings that need to be calculated at each SNP index) as well as the phasing time.

The rationale behind the deletion of low probability alternate phasings is that most ways of phasing a sample are unlikely to actually occur in nature, and phasing subsequent SNP indices are not likely to improve any given alternate phasing's probability of occurrence to merit its continued inclusion in the HMM model as more SNP indices are processed.

IV. Example and Evaluation

To evaluate the performance (e.g., accuracy and speed) of the phasing module 110, sets of most probable haplotype phasings for chromosomes from unrelated individuals were tested and compared against the true phasing. The true phase comes from the unambiguous sites (i.e., involving a homozygous SNP) of duo or trio-phased samples. A subset of these phased samples were then taken by removing individuals until there are no close relations (sharing more than 20 centimorgan (cM) of Identity by Descent (IBD) in the set. Related pairs were removed from the test sets because they do not provide independent accuracy results, and because unsupervised and semi-supervised phasing algorithms like HAPI-UR and Beagle artificially benefit from multiple haplotype instances. Because of the long running time of some of the experiments, all of experiments analyze chromosome 1 only (specifically, 52,129 pre-selected SNPs).

The performance of the phasing module 110 is compared against Beagle and to HAPI-UR. (See Sharon R. Browning and Brian L. Browning. Rapid and accurate haplotype phasing and missing-data inference for whole-genome association studies by use of localized haplotype clustering. *American Journal of Human Genetics*, 81:1084-1096, 2007; A. L. Williams A L, N. Patterson, J. Glessner, H. Hakonarson, and D. Reich. Phasing of many thousands of genotyped samples. *American Journal of Human Genetics*, 91:238-251, 2012.) Beagle is a semi-supervised approach that can benefit from a reference panel of phased samples. Several experiments are run using reference panels of various size (randomly sampled from test sets of samples). For this evaluation, Beagle version 3.3.2 was used with $n_{samples}$=20 for the default of 10 iterations. HAPI-UR is an unsupervised approach that is able to phase large input sets simultaneously and is more accurate the larger the input size. HAPI-UR version 1.01 was used with −w 84 (as is recommended by the manual) and default values for the other command-line parameters.

One test involved two such test sets of samples. The first set is 435 samples from the 1,000 Genomes project. (See R. M. Durbin, et. al. A map of human genome variation from population-scale sequencing. *Nature*, 467(7319):1061-1073, 2010.) The reference set R for the first test set consists of 217,171 samples. The second set is a proprietary set of 1,188 trio-phased samples. The reference set R for the second test set consists of 189503 samples. The second set is included because it is larger, contains a higher frequency of unambiguous SNPs of known phase (because all samples are trio—as opposed to duo-phased), and is much closer to a random sample of modern United States citizens.

The reference set R of haplotypes is generated by phasing with HAPI-UR (except for the imputation of missing data, which was done with Beagle), about 50,000 samples at a time, except for the samples where duo- or trio-information is available, in which case the samples are duo- or trio-phased by Beagle. Samples that are in either of the first or second test sets above, or that are a known relative of an individual in either of the test set samples are not included in the training set.

In this test, the phasing module 110 uses $\alpha=\beta=\frac{1}{2}$; C=20 (See Equation 1 above). The 260 Markov models used to phase the first test set were built in an average of 5 hours, 50 minutes; the longest time was 12 hours, 37 minutes. These times refer to building Markov models with a single-threaded computing process. The build time can be reduced somewhat by using multiple computing threads, each carrying out the algorithm described in Section II. The models used to phase the second test set used fewer training haplotypes and were built in less time (4 hours, 58 minutes on average). However, one advantage of the phasing process carried out by the phasing module 110 is that the Markov model-building process described in Section II need only be carried out once.

The results of the first test set are shown in Table 1, and the results of the second test set are shown in Table 2. These results show that the phasing module 110 achieves superior accuracy, and because it can phase each window in parallel, it can phase hundreds or thousands of samples in minutes, when the other programs take hours.

In the tables, supplementary input samples are the number of additional pre-phased reference samples, randomly-chosen from the reference set R, that are added to the program input to improve the phasing models. HAPI-UR treats them as unphased. The Markov models M are pre-computed by the Markov module 105 prior to testing, and the reference set R is not part of the input samples set U provided to the phasing application during the test. The model size is the number of states in the Beagle and Markov models. The total phase time is the running time of the program that phases the entire test set (and supplementary input samples if necessary) on chromosome 1. The phasing module 110 phases all samples in parallel, but the running time to phase them all serially is ordered for comparison. Phase flips are the average frequency of assigning adjacent heterozygous sites in a way that is inconsistent with the correct phase (as implied by duo and trio data associated with each test set sample). Impute error is the average rate of incorrect genotype imputation when 1% of genotypes are artificially removed at random from the test set.

TABLE 1

| Method | Supplementary Input Samples | Model | Total Phase Time | Phase Flips | Impute Error |
|---|---|---|---|---|---|
| Beagle | 0 | 1,569,682 | 1 h 9 m 18 s | 4.98% | 3.95% |
| Beagle | 1,000 | 5,019,777 | 3 h 8 m 37 s | 4.03% | 3.47% |
| Beagle | 2,000 | 8,071,534 | 5 h 21 m 20 s | 3.80% | 3.43% |
| Beagle | 5,000 | 16,497,840 | 18 h 50 m 38 s | 3.47% | 3.25% |
| HAPI-UR | 0 | N/A | 57 m 29 s | 18.70% | 54.09% |
| HAPI-UR | 10,000 | N/A | 11 h 4 m 48 s | 3.89% | 63.82% |
| HAPI-UR | 20,000 | N/A | 24 h 59 m 9 s | 3.46% | 63.17% |
| HAPI-UR | 50,000 | N/A | 3 d 4 h 42 m 7 s | 3.07% | 62.53% |
| System 100 | 0 | 117,063,292 | 3 m 0 s | 2.77% | 2.75% |
| (Markov Models M are pre-computed) | | | (4 h 11 m 8 s on a single processor) | | |

TABLE 2

| Method | Supplementary Input Samples | Model | Total Phase Time | Phase Flips | Impute Error |
|---|---|---|---|---|---|
| Beagle | 0 | 2,970,907 | 4 h 14 m 25 s | 2.60% | 2.23% |
| Beagle | 1,000 | 6,353,295 | 7 h 9 m 29 s | 2.09% | 1.91% |
| Beagle | 2,000 | 9,347,111 | 10 h 16 m 0 s | 1.90% | 1.85% |
| Beagle | 5,000 | 17,869,941 | 22 h 41 m 21 s | 1.63% | 1.67% |
| HAPI-UR | 0 | N/A | 2 h 44 m 17 s | 12.81% | 33.43% |
| HAPI-UR | 10,000 | N/A | 13 h 13 m 45 s | 2.00% | 44.27% |
| HAPI-UR | 20,000 | N/A | 1 d 3 h 13 m 29 s | 1.59% | 42.53% |
| HAPI-UR | 50,000 | N/A | 3 d 9 h 7 m 15 s | 1.23% | 40.23% |
| System 100 | 0 | 102,692,825 | 5 m 48 s | 0.93% | 1.09% |
| (Markov Models M are pre-computed) | | | (4 h 11 m 8 s on a single processor) | | |

The phasing processes described and discussed herein do not identically reproduce any known natural process that occurs in the real world, including those known to occur during DNA replication or cell division. Additionally, these phasing processes do not deterministically identify with perfect accuracy the correct phasing of a diploid genotype every single time a phasing is performed. Instead, the phasing techniques described herein, including not only those performed by the phasing module, but also by Beagle and HAPI-UR, provide probabilistic estimations regarding the most likely phasing of a diploid genotype. The phasing module 110 in particular, does not make this determination "from scratch" but instead bootstraps the result based on a known reference set R.

As such, these phasing processes, particularly those performed by the phasing module, are not known, natural processes, but instead are instead approximate calculations that estimate backwards to try and know and unknown quantity in the context of limited information, notably the situation where the genotype of an individual is known but not which haplotypes came from which parents. Beagle, HAPI-UR and the processes performed by the phasing module are all alternative methods of making these determinations. Each is different from the other in at least one way, and each has benefits and drawbacks that limit the utility of that particular technique. For example, the phasing process performed by the phasing module is limited in that it relies on a reference set R to arrive at its conclusions. Each is able to arrive at result (i.e., a most likely possible phasing for a diploid genotype) with a different amount of error and in a different amount of time. As discussed above, one of the major advantages of the phasing module's 110 approach over Beagle and HAPI-UR is reduced phasing time while maintaining comparable accuracy.

Using the example described above as a guide, given the quantities of genetic data used to build the Markov Models M, traverse the models to arrive at possible phasings and update the models, the number of iterations performed, and the number of calculations needed to perform each of the steps above, it should be clear that these computations are sufficiently complex so that it would be near impossible if not impossible for the human mind to complete these calculations in their lifetime. Computer processors, beneficially running in parallel, and computer memory are necessary to perform these operations in a practically useful amount of time.

V. Additional Considerations

Computing system 100 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1. In some embodiments, a distributed computing architecture is used to implement the described features. One example of such a distributed computing platform is the Apache Hadoop project available from the Apache Software Foundation.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "computing" or "determining" or the like refer to the action and processes of a computer system, or similar electronic computing device, that manipulates and transforms data represented as physical (electronic) quantities within the computer system memories or registers or other such information storage, transmission or display devices.

The algorithms and displays presented are not inherently related to any particular computer or other apparatus. Various general-purpose systems may also be used with programs in accordance with the teachings above, or it may prove convenient to construct more specialized apparatus to perform the required method steps. The required structure for a variety of these systems will appear from the description above. In addition, a variety of programming languages may be used to implement the teachings above.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

The invention claimed is:

1. A computer-implemented method for phasing diploid genotypes, the computer-implemented method comprising:
   accessing a set of reference haplotypes corresponding to reference diploid genotypes that have already been phased;
   accessing an input sample of a diploid genotype;
   iteratively updating, using one or more processors, a set of directed acyclic models based on the diploid genotype and the reference haplotypes, each directed acyclic model corresponding to a different window of single nucleotide polymorphisms (SNPs), at least one of the directed acyclic models comprising a set of nodes, wherein at least one node at a first level is a parent node that represents a particular haplotype sequence at the first level, the parent node having a first edge connected to a first sub node at a second level and a second edge connected to a second sub node at the second level, the first sub node representing a major allele at the second level and the second sub node representing a minor allele at the second level, and wherein iteratively updating the set of directed acyclic models comprises:
in each iteration,
applying the set of directed acyclic models to the input sample of the diploid genotype;
obtaining phasings of the input sample of the diploid genotype, the obtained phasing comprising a set of pairs of haplotypes of the input sample;
selecting, from the set of pairs of haplotypes of the input samples, a subset of pairs of haplotypes of the input samples;
updating the set of reference haplotypes by adding the selected subset of pairs of haplotypes of the input samples; and
updating at least one of the set of directed acyclic models using the updated set of reference haplotypes;
determining phasings of the diploid genotype using the one or more processors executing the set of directed acyclic models, the determining comprising:
applying the set of updated directed acyclic models to the input sample;
receiving output from each of the set of updated directed acyclic models, each output comprising at least a pair of phased haplotypes for the input sample; and
concatenating the received pairs of phased haplotypes to generate a single pair of phased haplotypes for the input sample; and
returning phased haplotypes for the input sample of the diploid genotype.

2. The computer-implemented method of claim 1, wherein determining phasings of the diploid genotype comprises:
generating, for each window, one or more haplotype phasing segments for the diploid genotype of that window based on one or more paths traversing the directed acyclic model for that window; and
combining the haplotype phasing segments for the windows into the phased haplotypes.

3. The computer-implemented method of claim 1, wherein each directed acyclic model is a Markov model.

4. The computer-implemented method of claim 1, wherein the at least one of the directed acyclic models comprises a merged node at the second level that is merged from two or more nodes at the second level.

5. The computer-implemented method of claim 4, wherein generating the merged node comprises:
accessing a plurality of candidate sub nodes at the second level;
for each pair of candidate sub nodes at the second level:
determining a first probability that a reference haplotype belongs to a first candidate sub node of the pair;
determining a second probability that the reference haplotype belongs to a first candidate sub node of the pair;
determining a difference between the first probability and the second probability; and
responsive to the difference being smaller than a threshold, merging the pair of candidate sub nodes into the merged node, the merged node comprising subsets of reference haplotypes represented by the first candidate sub node and the second candidate sub node.

6. The computer-implemented method of claim 5, further comprising:
responsive to the difference being at or larger than the threshold, not merging the pair of candidate sub nodes into the merged node.

7. The computer-implemented method of claim 1, wherein each edge is associated with a transition probability that represents a likelihood of an allele value associated with the edge.

8. The computer-implemented method of claim 7, wherein the transition probability of each edge is a value greater than 0.

9. The computer-implemented method of claim 7, wherein the transition probability of an edge of a sub node with a haplotype count of zero is nonzero.

10. A non-transitory computer readable medium for storing computer code comprising instructions, the instructions, when executed by one or more processors, cause the one or more processors to:
access a set of reference haplotypes corresponding to reference diploid genotypes that have already been phased;
access an input sample of a diploid genotype;
iteratively update, using one or more processors, a set of directed acyclic models based on the diploid genotype and the reference haplotypes, each directed acyclic model corresponding to a different window of single nucleotide polymorphisms (SNPs), at least one of the directed acyclic models comprising a set of nodes, wherein at least one node in a first level is a parent node that represents a particular haplotype sequence at the first level, the parent node having a first edge connected to a first sub node at a second level and a second edge connected to a second sub node at the second level, the first sub node representing a major allele for the second level and the second sub node representing a minor allele at the second level, and wherein iteratively updating the set of directed acyclic models comprises:
in each iteration,
applying the set of directed acyclic models to the input sample of the diploid genotype;
obtaining phasings of the input sample of the diploid genotype, the obtained phasing comprising a set of pairs of haplotypes of the input sample;
selecting, from the set of pairs of haplotypes of the input samples, a subset of pairs of haplotypes of the input samples;
updating the set of reference haplotypes by adding the selected subset of pairs of haplotypes of the input samples; and
updating at least one of the set of directed acyclic models using the updated set of reference haplotypes;
determine phasings of the diploid genotype using the one or more processor executing the set of directed acyclic models, wherein determining comprising:
applying the set of updated directed acyclic models to the input sample;
receiving output from each of the set of updated directed acyclic models, each output comprising at least a pair of phased haplotypes for the input sample; and
concatenating the received pairs of phased haplotypes to generate a single pair of phased haplotypes for the input sample; and
return phased haplotypes for the input sample of the diploid genotype.

11. The non-transitory computer readable medium of claim 10, wherein the instructions that cause the one or more processors to determine phasings of the diploid genotype comprise instructions that cause the one or more processors to:
generate, for each window, one or more haplotype phasing segments for the diploid genotype of that window based on one or more paths traversing the directed acyclic model for that window; and
combine haplotype phasing segments for the windows into the phased haplotypes.

12. The non-transitory computer readable medium of claim 10, wherein each directed acyclic model is a Markov model.

13. The non-transitory computer readable medium of claim 10, wherein the at least one of the directed acyclic models comprises a merged node at the second level that is merged from two or more nodes at the second level.

14. The non-transitory computer readable medium of claim 13, further comprising instructions that cause the one or more processors to:
access a plurality of candidate sub nodes at the second level;
for each pair of candidate sub nodes at the second level:
determine a first probability that a reference haplotype belongs to a first candidate sub node of the pair;
determine a second probability that the reference haplotype belongs to a first candidate sub node of the pair;
determine a difference between the first probability and the second probability; and
responsive to the difference being smaller than a threshold, merge the pair of candidate sub nodes into the merged node, the merged node comprising subsets of reference haplotypes represented by the first candidate sub node and the second candidate sub node.

15. The non-transitory computer readable medium of claim 14, further comprising:
responsive to the difference being at or larger than the threshold, not merging the pair of candidate sub nodes into the merged node.

16. The non-transitory computer readable medium of claim 10, wherein each edge is associated with a transition probability that represents a likelihood of an allele value associated with the edge.

17. The non-transitory computer readable medium of claim 16, wherein the transition probability of each edge is a value greater than 0.

18. The non-transitory computer readable medium of claim 16, wherein the transition probability of an edge of a sub node with a haplotype count of zero is nonzero.

19. A system comprising:
one or more processors; and
a memory storing instructions that when executed by the one or more processors cause the one or more processors to perform steps comprising:
accessing a set of reference haplotypes corresponding to reference diploid genotypes that have already been phased;
accessing an input sample of a diploid genotype;
iteratively updating, using one or more processors, a set of directed acyclic models based on the diploid genotype and the reference haplotypes, each directed acyclic model corresponding to a different window of single nucleotide polymorphisms (SNPs), at least one of the directed acyclic models comprising a set of nodes, wherein at least one node in a first level is a parent node that represents a particular haplotype sequence at the first level, the parent node having a first edge connected to a first sub node at a second level and a second edge connected to a second sub node at the second level, the first sub node representing a major allele for the second level and the second sub node representing a minor allele at the second level, and wherein iteratively updating the set of directed acyclic models comprises:
in each iteration,
applying the set of directed acyclic models to the input sample of the diploid genotype;
obtaining phasings of the input sample of the diploid genotype, the obtained phasing comprising a set of pairs of haplotypes of the input sample;
selecting, from the set of pairs of haplotypes of the input samples, a subset of pairs of haplotypes of the input samples;
updating the set of reference haplotypes by adding the selected subset of pairs of haplotypes of the input samples; and
updating at least one of the set of directed acyclic models using the updated set of reference haplotypes;
determining phasings of the diploid genotype using the one or more processor executing the set of directed acyclic models, the determining comprising:
applying the set of updated directed acyclic models to the input sample;
receiving output from each of the set of updated directed acyclic models, each output comprising at least a pair of phased haplotypes for the input sample; and
concatenating the received pairs of phased haplotypes to generate a single pair of phased haplotypes for the input sample; and
returning phased haplotypes for the input sample of the diploid genotype.

20. The system of claim 19, wherein the instructions that cause the one or more processors to determine phasings of the diploid genotype comprise instructions that cause the one or more processors to perform steps comprising:
generating, for each window, one or more haplotype phasings segments for the diploid genotype of that window based on one or more paths traversing the directed acyclic model for that window; and
combining the haplotype phasing segments for the windows into the phased haplotypes.

* * * * *